United States Patent [19]

Chekroun et al.

[11] Patent Number: 5,405,960
[45] Date of Patent: Apr. 11, 1995

[54] TRIARYLBORANE DERIVATIVES, THEIR PREPARATION AND THEIR USE AS SYNTHESIS INTERMEDIATES

[75] Inventors: Isaac Chekroun, Epinay; Guy Rossey, Voisins le Bretonneux; Michel Magnat, Poissy, all of France

[73] Assignee: Synthelabo, Le Plessis Robinson, France

[21] Appl. No.: 288,192

[22] Filed: Aug. 9, 1994

Related U.S. Application Data

[62] Division of Ser. No. 166,026, Dec. 14, 1993.

Foreign Application Priority Data

Nov. 26, 1993 [FR] France .................. 93.14152

[51] Int. Cl.$^6$ .................. C07D 257/04; C07D 237/28
[52] U.S. Cl. .................. 544/235; 544/237; 544/284; 544/298; 544/322; 544/333; 544/334; 544/335; 546/14; 546/139; 546/141; 546/143; 546/276; 548/110; 548/250; 548/252; 548/254
[58] Field of Search .............. 548/110, 250, 252, 254; 544/235, 237, 284, 298, 322, 333, 334, 335; 546/14, 139, 141, 143, 276

[56] References Cited

U.S. PATENT DOCUMENTS

| | | | |
|---|---|---|---|
| 5,130,439 | 7/1992 | Lo et al. | 548/110 |
| 5,310,928 | 5/1994 | Lo et al. | 548/250 |

*Primary Examiner*—Mary C. Lee
*Assistant Examiner*—Joseph K. McKane
*Attorney, Agent, or Firm*—Jacobson, Price, Holman & Stern

[57] ABSTRACT

Triarylborane derivatives corresponding to the formula (1)

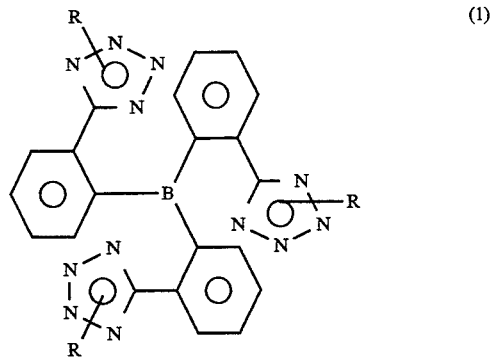

in which

R either represents a group —$CR_1R_2R_3$ where $R_1$, $R_2$ and $R_3$ are each, independently of one another, a ($C_1$–$C_2$)alkyl or aryl group, or represents a group —$CH_2OR_4$ where $R_4$ is a ($C_1$–$C_2$)alkyl or benzyl group, or represents a group —$Si(R_5)_3$ where $R_5$ is a ($C_1$–$C_2$)alkyl or aryl group, R being in the 1 or 2 position of the tetrazole ring, their preparation and their use as synthesis intermediates.

6 Claims, No Drawings

TRIARYLBORANE DERIVATIVES, THEIR PREPARATION AND THEIR USE AS SYNTHESIS INTERMEDIATES

This is a divisional application of Ser. No. 08/166,026, filed Dec. 14, 1993.

The present invention relates to triarylborane derivatives corresponding to the formula (1)

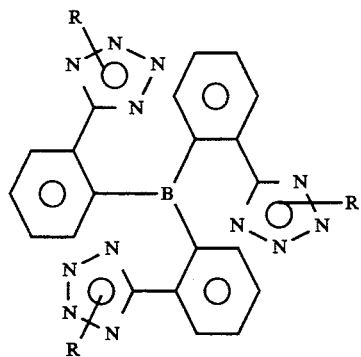

in which

R either represents a group —$CR_1R_2R_3$ where $R_1$, $R_2$ and $R_3$ are each, independently of one another, a ($C_1$–$C_2$)alkyl or aryl group, or represents a group —$CH_2OR_4$ where $R_4$ is a ($C_1$–$C_2$)alkyl or benzyl group, or represents a group —$Si(R_5)_3$ where $R_5$ is a ($C_1$–$C_2$)alkyl or aryl group, R being in position 1 or 2 of the tetrazole ring, their preparation and their use in aryl-aryl, aryl-naphthyl, aryl-heteroaryl or aryl-(fused heteroaryl) couplings in the presence of catalysts based on transition metals and, in particular, on palladium.

The preferred compounds according to the invention are the compounds corresponding to the formula (1) in which R is a 1,1-dimethylethyl group.

According to the invention, the compounds of formula (1) can be prepared from derivatives of formula (2) in which R is as defined above and Z represents either a hydrogen atom or a halogen atom such as, for example, a bromine, chlorine or iodine atom, according to the scheme below. The compound of formula (2) is reacted with an alkyllithium such as n-butyllithium or hexyllithium or lithiated hexamethyldisilazane, in an aprotic solvent such as tetrahydrofuran, at a temperature between 20° C. and the reflux temperature. An organolithium compound is obtained, which is reacted with a tri($C_1$–$C_4$)alkyl borate or a trihaloborane such as, for example, boron trichloride or boron tribromide, in a solvent such as tetrahydrofuran.

Scheme

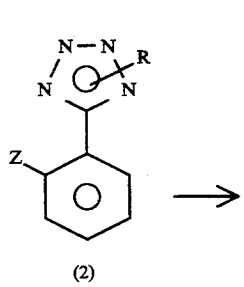

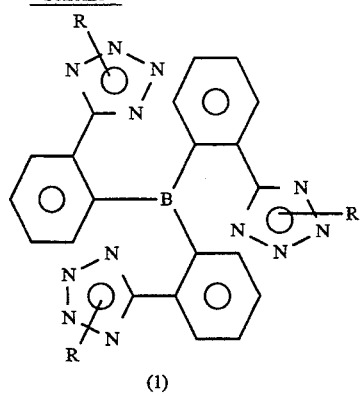

In a variant of the process, an organomagnesium compound is prepared from a compound of formula (2) in which Z represents a halogen atom, and the procedure is then as described above.

The starting compounds are commercially available or described in the literature, or may be prepared according to methods which are described therein or which are known to a person skilled in the art.

Thus, 2-(1,1-dimethylethyl)-5-phenyltetrazole is prepared according to the method described for an analogous derivative by J. W. Tilley et al. *J. Med. Chem.* 1991, 34, 1125–1126.

The triarylborane derivatives thus obtained are stable solids which may be coupled with aromatic or heteroaromatic halides containing numerous substituents such as, for example, alkyl, hydroxymethyl, aminomethyl, alkoxymethyl, carboxamide, carbonyl, carboxyl, cyano, alkoxy, nitro or methyl groups substituted with various heterocyclic units. These couplings may be carried out in an aqueous-organic medium.

The 1,1-dimethylethyl group is a protecting group which is particularly stable under various reaction conditions encountered in organic chemistry. Its use as a protecting group of the tetrazolyl function permits the use of the compounds of the invention and of the products resulting therefrom, in various chemical conversion reactions.

The following example illustrates the preparation of compounds according to the invention.

The microanalyses and the IR and NMR spectra confirm the structure of the compounds obtained.

EXAMPLE 5,5′,5″-[borylidynetris(1,2-phenylene)]tris [2-(1,1-dimethylethyl)-2H-tetrazole]

Into a 100 ml three-necked round-bottomed flask maintained under a nitrogen atmosphere are introduced 5 g (25 mmol) of 2-(1,1-dimethylethyl)-5-phenyl-2H-tetrazole and 20 ml of anhydrous tetrahydrofuran, and 13 ml of a 2.5M solution of n-butyllithium in hexane are then added dropwise over a period of 30 minutes. The mixture is brought to the reflux temperature and 1.4 ml (12 mmol) of trimethyl borate are added over a period of 4 hours. The solvents are evaporated off under vacuum and the residue is taken up in 50 ml of ethyl acetate and washed with water. The solvent is evaporated off to give an oily residue which is triturated in methanol, and the precipitate formed is recovered. It is filtered off and dried under vacuum.

3.5 g of product are obtained.

Melting point =230° C.

The compounds according to the invention may be used for the synthesis of compounds corresponding to the formula (I)

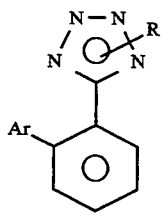

in which Ar represents either an aryl group, or a heteroaryl group such as, for example, pyridyl or pyrimidinyl groups, or a naphthyl group, or a fused heteroaryl group such as, for example, quinoline, isoquinoline, phthalazine, cinnoline, quinazoline, benzofuran, benzothiophene, indole, benzothiazole, benzoxazole or benzimidazole groups, which may be optionally substituted with an alkyl, aminomethyl, hydroxymethyl, alkoxymethyl, alkoxy, carboxamide, carbonyl, carboxyl, cyano, nitro or methyl group substituted with various heterocyclic units such as, for example, an imidazolyl, pyridyl, pyrimidinyl, imidazopyridyl, triazolopyrimidinyl or pyrazolopyrimidine group, and R is as defined above.

The compounds of formula (I) are intermediates in the synthesis of compounds which are angiotensin II antagonists, such as those described in European Patent Applications 0,253,310, 0,324,377, 0,401,030, 0,407,342, 0,424,317, 0,500,409, 0,522,038, 0,540,400 and in European Patent 0,521,768.

The synthesis of the compounds of formula (I) from the compounds of the invention is carried out according to one of the methods described below. A derivative of formula (1) is reacted with a derivative of general formula Ar-Z in which Z is a halogen atom or a group $-OSO_2CF_3$ and Ar is as defined above, in the presence of a base such as, for example, sodium carbonate, potassium carbonate, potassium dihydrogen phosphate or a tertiary amine such as triethylamine and a catalyst based on palladium complexed with a phosphine, such as triphenylphosphine, 1,2-bis-(diphenylphosphino)ethane or 1,2-bis-(diphenylphosphino)propane, in a solvent such as, for example, toluene, xylene, dimethylformamide, N-methylpyrrolidinone, methanol, ethanol, butanol, isopropanol, 1,1-dimethylethanol or isoamyl alcohol, pure or in the presence of water.

The examples below illustrate the synthesis of the compounds of formula (I) from the compounds of formula (1) of the invention.

A   2'-[2-(1,1-dimethylethyl)-2H-tetrazol-5-yl][1,1'-biphenyl]-4-carboxaldehyde

Into a 50 ml three-necked round-bottomed flask maintained under a nitrogen atmosphere are introduced 1.1 g (1.79 mmol) of 5,5',5"-borylidynetris (1,2-phenylene)]tris [2-(1,1-dimethylethyl)-2H-tetrazole] prepared according to the method described in the preceding example, 0.9 g (4.9 mmol) of 4-bromobenzaldehyde, 1.4 g of potassium carbonate, 0.17 g (0.15 mmol) of tetrakis(triphenylphosphine)palladium, 20 ml of N,N-dimethylformamide and 2.5 ml of water. The mixture is heated to 85° C. for 1 hour and then poured into 100 ml of water. The product is then extracted twice with 50 ml of ethyl acetate and the organic phases are combined. They are washed with water and dried over sodium sulfate and the solvent is evaporated off to dryness. An oily residue is obtained which crystallizes upon trituration in cyclohexane. The solid thus obtained is recovered, filtered and dried under vacuum.

1.2 g of product are obtained.

Melting point =70° C.

B   6-butyl-2-(2-phenylethyl)-5-{[2'[2-(1,1-dimethylethyl)-2H-tetrazol-5-yl][1,1'-biphenyl]-4-yl]methyl} pyrimidin-4(3H)-one 1st method Into a 50 ml three-necked round-bottomed flask maintained under a nitrogen atmosphere are introduced 0.94 g (1.52 mmol) of 5,5',5"-[borylidynetris(1,2-phenylene)]tris[2-(1,1-dimethylethyl)-2H-tetrazole] prepared according to the method described above, 1.7 g (4 mmol) of 5-[(4-bromophenyl)methyl]-6-butyl-2-(2-phenylethyl)pyrimidin-4(3H)-one, 0.9 g (8 mmol) of potassium 1,1-dimethylethylate, 0.14 g (0.121 mmol) of tetrakis(triphenylphosphine)palladium and 17 ml of 1,1-dimethylethanol. The reaction mixture is heated for 10 hours at the reflux temperature, diluted with 25 ml of water and extracted successively with 40 ml and then with 20 ml of ethyl acetate. The organic phases are combined, washed with water and dried over sodium sulfate and the solvent is evaporated off to dryness. An oily residue is obtained which crystallizes upon trituration in 5 ml of methanol. The solid thus obtained is recovered, filtered and dried under vacuum.

1.43 g of product are obtained.

Melting point =144° C.

2nd method 1 g (1.62 mmol) of 5,5',5"-[borylidynetris-(1,2-phenylene)]tris[2-(1,1-dimethylethyl)-2H-tetrazole] prepared according to the method described above, 2 g (5 mmol) of 5-[(4-bromophenyl)methyl]-6-butyl-2-(2-phenylethyl)pyrimidin-4(3H)-one, 0.163 g (0.140 mmol) of tetrakis(triphenylphosphine)palladium, 4.7 ml of a 2M sodium carbonate solution in water and 20 ml of toluene are heated at the reflux temperature for 4 hours. The mixture is left to cool, the aqueous phase is removed and the organic phase is collected. It is washed with water and dried over sodium sulfate and the solvent is evaporated off to dryness. The residue is triturated in ethanol, and the solid thus obtained is recovered, filtered and dried under vacuum.

1.1 g of product in the form of a white solid are obtained.

Melting point =143° C.

3rd method

Into a 100 ml three-necked round-bottomed flask maintained under a nitrogen atmosphere are introduced 1 g (1.62 mmol) of 5,5',5"-[borylidynetris(1,2-phenylene)]tris[2-(1,1-dimethylethyl)-2H-tetrazole] prepared according to the method described above, 2 g (5 mmol) of 5-[(4-bromophenyl)methyl]-6-butyl-2-(2-phenylethyl)pyrimidin-4(3H)one, 0.163 g (0.140 mmol) of tetrakis(triphenylphosphine)palladium, 1.3 g of potassium carbonate, 20 ml of N,N-dimethylformamide and 5 ml of water. The reaction medium is heated to 85° C. for 3 hours and then poured into 100 ml of water. It is then extracted with ethyl acetate, the organic phase is washed with water and dried over sodium sulfate and the solvent is evaporated off to dryness. An oily residue is obtained which crystallizes upon trituration in methanol. The solid thus obtained is recovered, filtered and dried under vacuum.

1.7 g of product in the form of a white solid are obtained.

Melting point = 145° C.

The process according to the invention makes it possible to obtain compounds of formula (I) of high purity in good yield.

It makes possible the coupling of aromatic and heteroaromatic halides or trifluoromethanesulfonyloxy analogs containing a variety of organic functions such as, for example, alcohols, ethers, amines, aldehydes, ketones, acids, esters, nitriles, amides and nitrated or sulfur-containing derivatives.

Moreover this process avoids the use of explosive azides and contributes to the protection of the environment (recycling of the palladium).

We claim:

1. A method for the synthesis of the compounds corresponding to the formula (I)

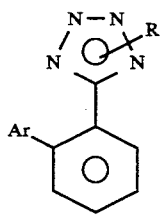

in which Ar represents an aryl group, a heteroaryl group, a naphthyl group, or a fused heteroaryl group which may be optionally substituted with an alkyl, aminomethyl, hydroxymethyl, alkoxymethyl, alkoxy, carboxamide, carbonyl, carboxyl, cyano, nitro or methyl group substituted with various heterocyclic units and R is a —CR$_1$R$_2$R$_3$ group where R$_1$, R$_2$ and R$_3$ are each, independently of one another, a (C$_1$-C$_2$)alkyl or aryl group, or a —CH$_2$OR$_4$ group where R$_4$ is a (C$_1$-C$_2$)alkyl or benzyl group, or represents a —Si(R$_5$)$_3$ group where R$_5$ is a (C$_1$-C$_2$)alkyl or aryl group, comprising reacting a triarylborane derivative corresponding to the formula (1)

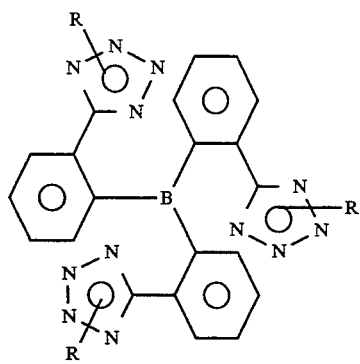

in which
R is as defined above and is in position 1 or 2 of the tetrazole ring, with a compound of general formula Ar-Z in which Z is a halogen atom or a group —OSO$_2$CF$_3$ and Ar is as defined above in the presence of a catalyst based on palladium complexed with a phosphine in a solvent.

2. The method as claimed in claim 1 in which Ar is pyridyl, pyrimidinyl, quinoline, isoquinoline, phthalazine, cinnoline, quinazoline, benzofuran, benzothiophene, indole, benzothiazole, benzoxazole or benzimidazole and the various heterocyclic units are imidazopyridyl, triazolopyrimidinyl or pyrazolopyrimidine.

3. The method as claimed in claim 1 in which the triarylborane derivative is reacted with a compound of general formula Ar-Z in the presence of a base or a tertiary amine.

4. The method as claimed in claim 3 in which the base is sodium carbonate, potassium carbonate, or potassium dihydrogen phosphate and the tertiary amine is triethylamine.

5. The method as claimed in claim 3 in which the catalyst is triphenylphosphine, 1,2-bis-(diphenylphosphino)ethane or 1,2-bis-(diphenylphosphino)propane.

6. The method as claimed in claim 3 in which the solvent is toluene, xylene, dimethylformamide, N-methylpyrrolidinone, methanol, ethanol, butanol, isopropanol, 1,1-dimethylethanol or isoamyl alcohol, alone or in the presence of water.

* * * * *